(12) United States Patent
Hsieh

(10) Patent No.: US 6,529,574 B1
(45) Date of Patent: Mar. 4, 2003

(54) METHODS AND APPARATUS FOR FOV-DEPENDENT ALIASING ARTIFACT REDUCTION

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 19 days.

(21) Appl. No.: 09/908,356

(22) Filed: Jul. 18, 2001

(51) Int. Cl.$^7$ .............................................. A61B 6/03
(52) U.S. Cl. ................................... 378/4; 378/901
(58) Field of Search .................... 378/4, 8, 15, 19, 378/901

(56) References Cited

U.S. PATENT DOCUMENTS

| | | | |
|---|---|---|---|
| 4,885,688 A | * 12/1989 | Crawford | ............. 345/427 |
| 5,243,284 A | 9/1993 | Noll | |
| 5,301,266 A | 4/1994 | Kimura | |
| 5,657,402 A | 8/1997 | Bender et al. | |
| 5,774,601 A | 6/1998 | Mahmoodi | |
| 6,072,851 A | * 6/2000 | Sivers | ............. 378/15 |
| 6,181,832 B1 | 1/2001 | Maas, III | |
| 6,233,308 B1 | 5/2001 | Hsieh | |
| 6,269,176 B1 | 7/2001 | Barski et al. | |
| 6,285,732 B1 | 9/2001 | Hsieh | |

* cited by examiner

Primary Examiner—David V. Bruce
(74) Attorney, Agent, or Firm—Carl B. Horton, Esq.; Armstrong Teasdale LLP

(57) ABSTRACT

In one aspect, there is provided a method for reducing aliasing artifacts in a computed tomography system. The method includes scanning an object with a computed tomography system to acquire a projection data set of measured views; synthesizing additional views of the projection data set utilizing view interpolation; and filtering and backprojecting the projection data set utilizing a weighting function dependent upon parameters $R_f$ and $R_t$, where radius $R_f$ around an isocenter of the CT imaging system is selected in accordance with a low artifact criterion and $R_t$ is a parameter defining a transition region outside of radius $R_f$ around the isocenter of the CT imaging system.

40 Claims, 5 Drawing Sheets

ND APPARATUS FOR
METHODS AND APPARATUS FOR FOV-DEPENDENT ALIASING ARTIFACT REDUCTION

BACKGROUND OF THE INVENTION

This invention relates generally to methods and apparatus for computed tomographic (CT) imaging of an object, and more particularly to method and apparatus for reducing artifacts and increasing spatial resolution at high scan rates in sampling rate limited CT imaging systems.

To avoid view aliasing artifacts, data-sampling rates must be increased proportionately for faster CT scan speeds. As an example, if a data acquisition system (DAS) sampling rate is sufficient at 984 Hz for a 1.0 second scan speed, the DAS sampling rate must be at least 984/x for a CT scanner that rotates at x seconds per revolution. Accordingly, the DAS sampling rate must be at least 1968 Hz for a 0.5 second scan speed. In one known scanning system, the DAS sampling rate is limited to 1408 Hz. For a fixed number of projections, the sampling density in the azimuthal direction decreases with an increase in distance from an iso-center. Thus, at 0.5 second scan speeds, this is a view deficiency in such systems caused by a lack of adequate samples in an azimuthal direction. This view deficiency results in aliasing artifacts and reduced spatial resolution.

BRIEF SUMMARY OF THE INVENTION

There is therefore provided, in one aspect, a method for reducing aliasing artifacts in a computed tomography system. The method includes scanning an object with a computed tomography system to acquire a projection data set of measured views; synthesizing additional views of the projection data set utilizing view interpolation; and filtering and backprojecting the projection data set utilizing a weighting function dependent upon parameters $R_f$ and $R_t$, where radius $R_f$ around an isocenter of the CT imaging system is selected in accordance with a low artifact criterion and $R_t$ is a parameter defining a transition region outside of radius $R_f$ around the isocenter of the CT imaging system.

In another aspect, a method for reducing aliasing artifacts in a computed tomography system is provided that includes scanning an object with a computed tomography (CT) imaging system to acquire a projection data set of measured views; reconstructing a first image utilizing the measured views to produce an image having a central, essentially artifact-free zone; interpolating views between measured views to produce a projection data set having interpolated views; reconstructing a second image utilizing the interpolated views; and producing a blended image from the first image and the second image utilizing a weighting function selected to smoothly transition from the first image to the second image in a transition region surrounding an isocenter of the CT imaging system.

In still another aspect, there is provided a computed tomographic (CT) imaging system having a rotating gantry, a detector array on the rotating gantry, and a radiation source on the rotating gantry configured to project a beam of radiation towards the detector array through an object to be imaged. The system is configured to scan an object to acquire a projection data set of measured views; synthesize additional views of the projection data set utilizing view interpolation; and filter and backproject the projection data set utilizing a weighting function dependent upon parameters $R_f$ and $R_t$, where radius $R_f$ around an isocenter of the CT imaging system is selected in accordance with a low artifact criterion and $R_t$ is a parameter defining a transition region outside of radius $R_f$ around the isocenter of the CT imaging system.

In yet another aspect, there is provided a computed tomographic (CT) imaging system having a rotating gantry, a detector array on the rotating gantry, and a radiation source on the rotating gantry configured to project a beam of radiation towards the detector array through an object to be imaged. The system is configured to scan an object to acquire a projection data set of measured views; reconstruct a first image utilizing the projection data set of measured views to produce an image having a central, essentially artifact-free zone; interpolate views between measured views of the projection data set of measured views to produce a projection data set having interpolated views; reconstruct a second image utilizing the interpolated views; and produce a blended image from the first image and the second image utilizing a weighting function selected to smoothly transition from the first image to the second image in a transition region surrounding an isocenter of the CT imaging system.

In still another aspect, there is provided a computer configured to read a projection data set of measured views obtained by scanning an object with a computed tomographic (CT) imaging system; synthesize additional views of the projection data set utilizing view interpolation; and filter and backproject the projection data set utilizing a weighting function dependent upon parameters $R_f$ and $R_t$, where radius $R_f$ around an isocenter of the CT imaging system is selected in accordance with a low artifact criterion and $R_t$ is a parameter defining a transition region outside of radius $R_f$ around the isocenter of the CT imaging system.

In yet another aspect, there is provided a computer readable medium having recorded thereon instructions configured to read a projection data set of measured views obtained by scanning an object with a computed tomographic imaging system; reconstruct a first image utilizing the projection data set of measured views to produce an image having a central, essentially artifact-free zone; interpolate views between measured views to produce a projection data set having interpolated views; reconstruct a second image utilizing the interpolated views; and produce a blended image from the first image and the second image utilizing a weighting function selected to smoothly transition from the first image to the second image in a transition region surrounding an isocenter of the CT imaging system.

It will be observed that embodiments of the present invention result in reduced aliasing artifacts and increased spatial resolution for scan rates that would otherwise require increased data acquisition system sampling rates.

DETAILED DESCRIPTION OF THE INVENTION

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
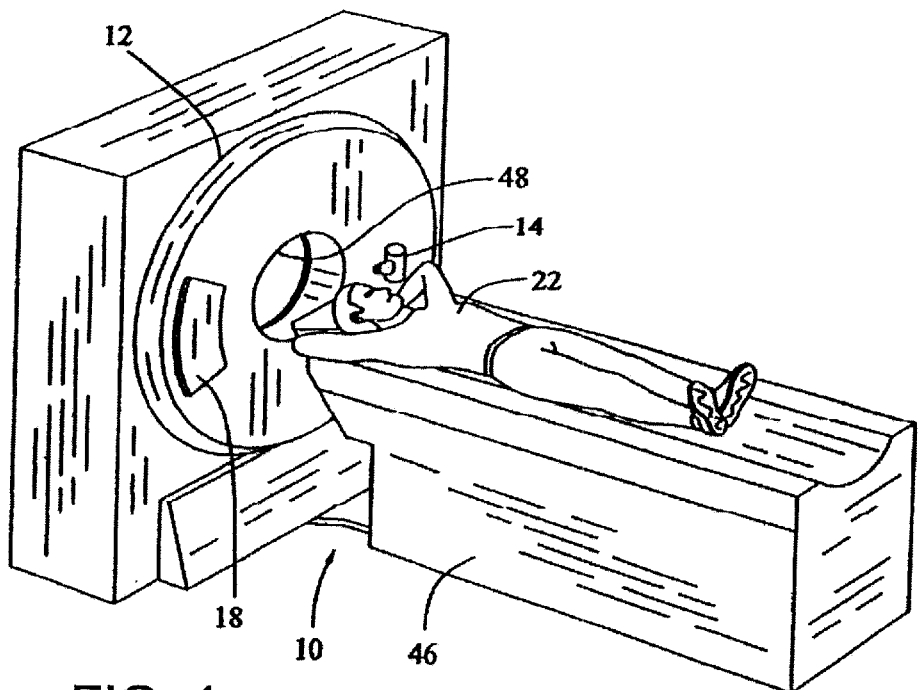
FIG. 1 is a pictorial view of a CT imaging system.
Figure 2:
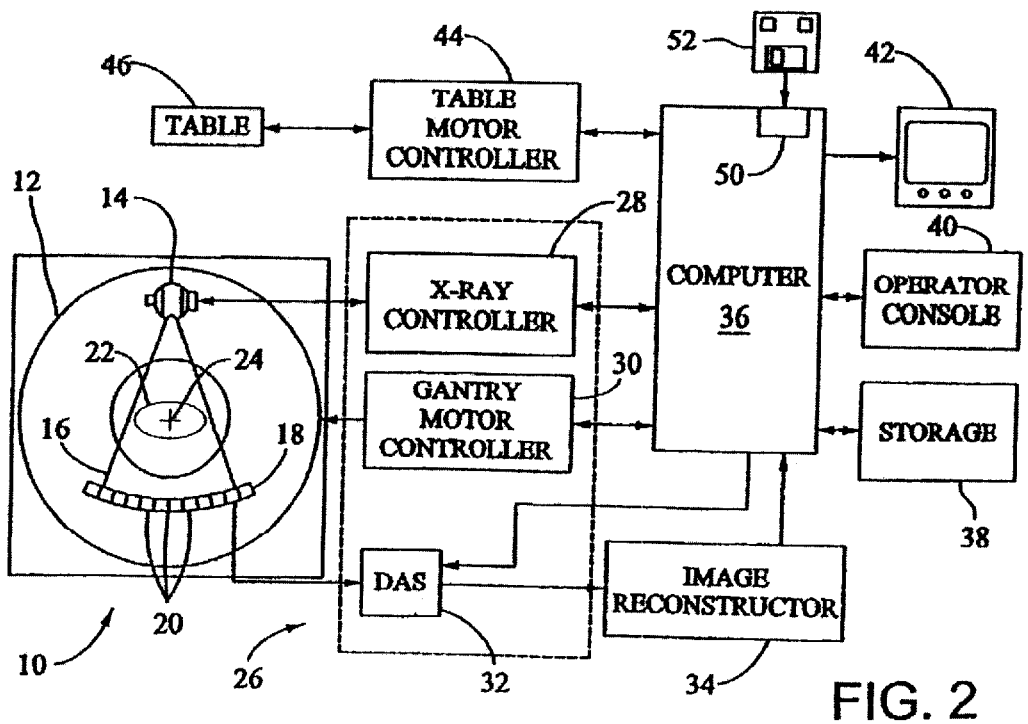
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray radiation source 14 that projects a beam of x-ray radiation 16 toward a detector array 18 on the opposite side of gantry 12. Detector array 18 is formed by detector elements 20 that together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. In one embodiment, detector array 18 is fabricated in a multi-slice configuration. In a multi-slice configuration, detector array 18 has a plurality of rows of detector elements or cells 20, only one of which is shown in FIG. 2. One or more additional rows of detector elements 20 in such configurations are arranged parallel to the illustrated row, and each row is transverse to the translation direction of patient 22 (i.e., the z-axis or patient axis).

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements or cells 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38. Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In a helical scan as performed in one embodiments of the present invention, table 46 moves while projection data is being collected and gantry 12 is rotating. The "helical pitch" is a measure of the amount of movement of table 46 per rotation of gantry 12. In an axial scan as performed in one embodiment of the present invention, table 46 is stationary while projection data is being acquired and gantry 12 is rotating.

In one embodiment, computer 36 includes a device 50 for reading and writing onto removable media 52. For example, device 50 is a floppy disk drive, a CD-R/W drive, or a DVD drive. Correspondingly, media 52 is either a floppy disk, a compact disk, or a DVD. Device 50 and media 52 are used in one embodiment to transfer acquired projection data from imaging system 10 to another computer for further processing, or in another embodiment to input machine readable instructions that are processed by computer 36.

View aliasing is caused mainly by a lack of adequate samples in an azimuthal direction. For a fixed number of projections, a sampling density in the azimuthal direction decreases with an increase in distance from an isocenter. For example, although a 984 Hz sampling rate is insufficient to ensure adequate sampling density near edges of a 50 cm FOV for a 0.5 scan speed, this rate is still sufficient to provide adequate sampling within a 25 cm FOV. That this rate is sufficient can be shown by observing that for a 1 second scan speed, an azimuthal sampling distance between adjacent views at the edge of a 50 cm FOV for a 1 second scan is $50\pi/984$. With the same DAS 32 sampling rate, a 0.5 second scan speed provides 492 views per revolution. Therefore, a sampling distance in an azimuthal direction at an edge of a 25 cm FOV is $25\pi/492=50\pi/984$. This sampling density is identical to a sampling density for a 1 second scan, which is sufficient to provide acceptably low view aliasing. As a result, a 0.5 second scan provides an artifact-free zone for a 0.5 second scan inside a center 25 cm FOV. In other words, no aliasing artifact correction is required inside the center 25 cm FOV.

Figure 3:
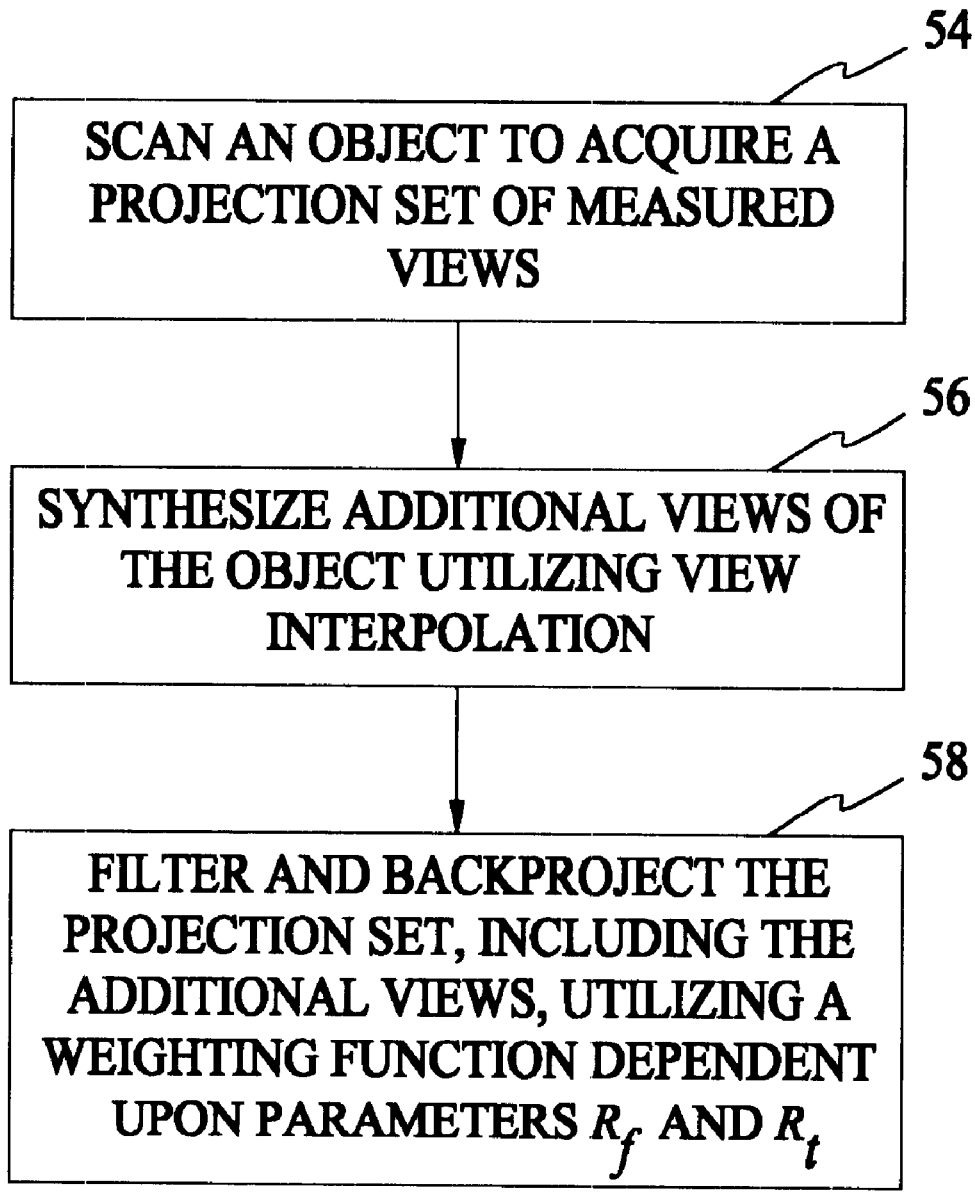
FIG. 3 is a simplified flow chart representative of one embodiment of the present invention.

Thus, in one embodiment and referring to FIG. 3, an alias artifact reduction algorithm is provided that is field of view (FOV) and reconstruction algorithm dependent. In particular, an object 22 is scanned 54 with CT imaging system 10 to acquire a projection data set of measured views. Additional views of the projection data set are synthesized 56 utilizing view interpolation. The projection data set, including the interpolated views and the measured views, is filtered and backprojected 58 utilizing a weighting function dependent upon parameters $R_f$ and $R_t$. Here, $R_f$ is a radius around an isocenter 24 of CT imaging system 10 selected in accordance with a low artifact criterion, and $R_t$ is a parameter defining a transition region outside of radius $R_f$. In one embodiment, the weighting function is different for measured views and synthesized views of the projection data set.

Figure 4:
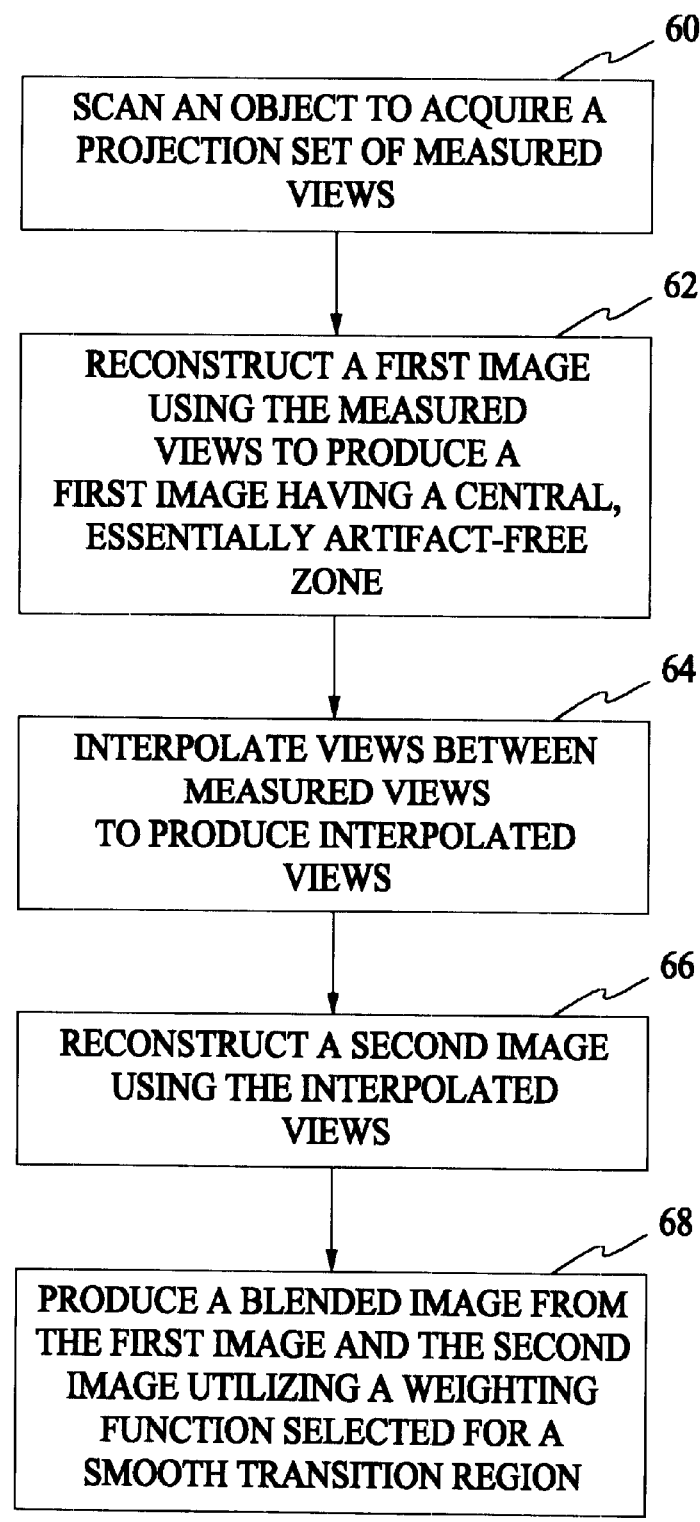
FIG. 4 is a simplified flow chart representative of another embodiment of the present invention.

In another embodiment and referring to FIG. 4, an object is scanned 60 with a CT imaging system 10 to acquire a projection data set of measured views. A first image is reconstructed 62 utilizing the measured views to produce an image having a central, essentially artifact-free zone. Views between measured views of the projection data set are interpolated 64 to produce a projection data set having interpolated views. A second image is reconstructed 66 utilizing the interpolated views. (Interpolated views are not included in the reconstruction of the first image.) A blended image is produced 68 from the first image and the second image utilizing a weighting function selected to smoothly transition from the first image to the second image in an annular transition region surrounding isocenter 24 of CT imaging system 10. In one embodiment, a radius $R_f$ of the central, essentially artifact-free zone is determined based on the sampling rate of DAS 32, the scan speed (i.e., gantry 12 rotation rate) of imaging system 10, and the image reconstruction algorithms used (i.e., higher resolution kernels permit higher frequency contents to be preserved).

Figure 5:
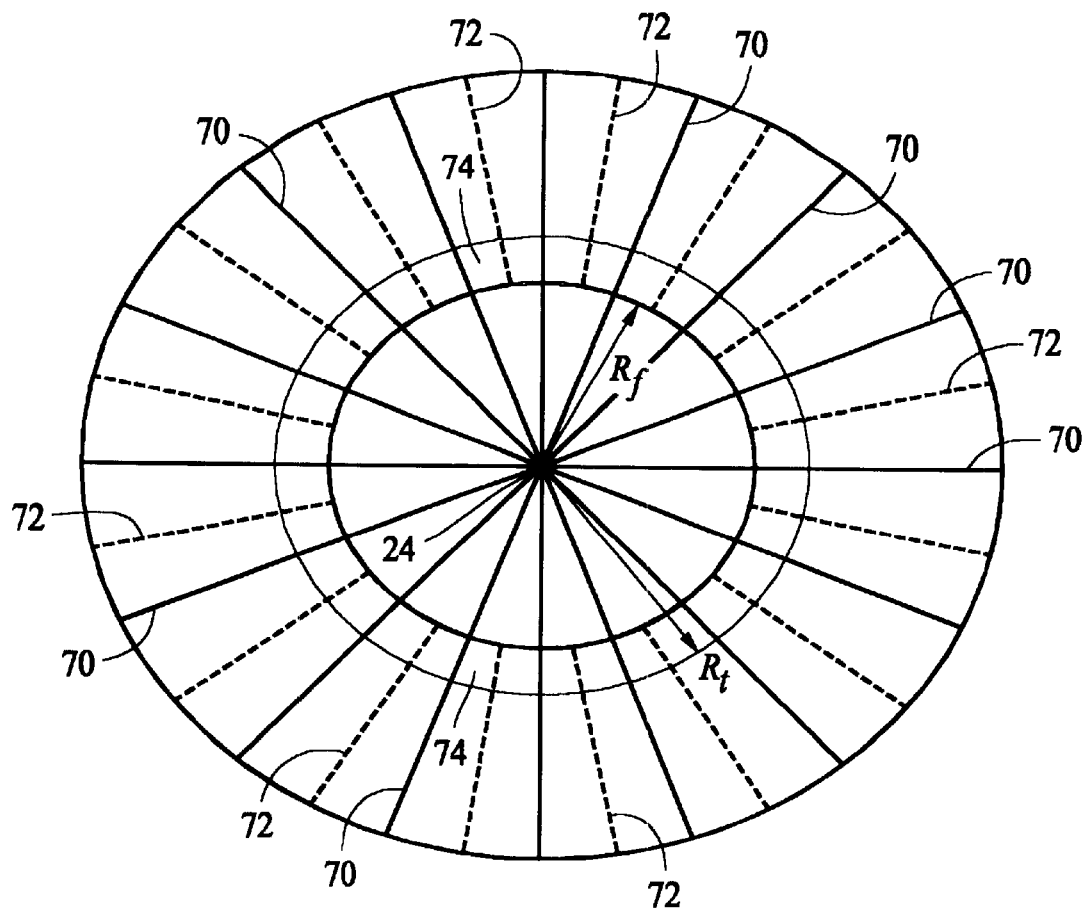
FIG. 5 is a pictorial representation of imaging blending showing two image regions and solid lines representing acquired projection data and dashed lines representing synthesized data samples.

For example and referring to FIG. 5, let $R_f$ be the radius of the aliasing artifact-free (or nearly artifact-free) zone. For the measured views, represented by solid lines 70, a first image $P_1$ is reconstructed. A view interpolation is performed, for example, by synthesizing views 72 uniformly in all directions or by synthesizing views utilizing an adaptive method.

The projection data set of interpolated views produced either adaptively or by uniform synthesis is used to reconstruct a second image $P_2$. The two images $P_1$ and $P_2$ are combined using weighting functions written as:

$$P(i,j)=w_1(i,j)P_1(i,j)+w_2(i,j)P_2(i,j),$$

where the sum of weights $w_1(i,j)$ and $w_2(i,j)$ is a constant, for example, unity [i.e., $w_1(i,j)=1-w_2(i,j)$], and $w_2(i,j)$ increases in magnitude relative to $w_1(i,j)$ at least within a transition region in a vicinity of radius $R_f$. For example, with the normalization $w_1(i,j)=1-w_2(i,j)$, one suitable function $w_2(i,j)$ is written:

$$w_2(i,j) = \begin{cases} 0, & r \le R_f \\ \frac{r-R_f}{2(R_t-R_f)} & R_f < r \le R_t \\ 0.5 & r > R_t. \end{cases}$$

Here, r is a distance of pixel (i,j) from isocenter 24 and $R_t$ is a parameter that determines transition region 74, which is dependent upon DAS 32 sampling rate, reconstruction kernel, and scan speed. Parameter $R_t$, in one embodiment, is determined experimentally.

In another embodiment, a similar method is applied directly as part of the backprojection. In this embodiment, it is not necessary to generate two separate images. Instead, an additional weighting function is used during backprojection. The weighting function is a function of $R_f$ and $R_t$. The weighting functions for measured views and synthesized views are different.

In another embodiment, second image $P_2$ is reconstructed utilizing both the measured views and the interpolated views. Images $P_1$ and $P_2$ are combined using weighting functions $w_1(i,j)$ and $w_2(i,j)$ written differently from those above. The resulting image P(i,j) is written:

$$P(i,j)=w_1(i,j)P_1(i,j)+w_2(i,j)P_2(i,j)$$

where:

$$w_1(i,j)=-i\, w_2(i,j)$$

and $$w_2(i,j) = \begin{cases} 0 & r \le R_f \\ \frac{r-R_f}{R_t-R_f} & R_f < r \le R_t \\ 1 & r > R_t. \end{cases}$$

Figure 6:
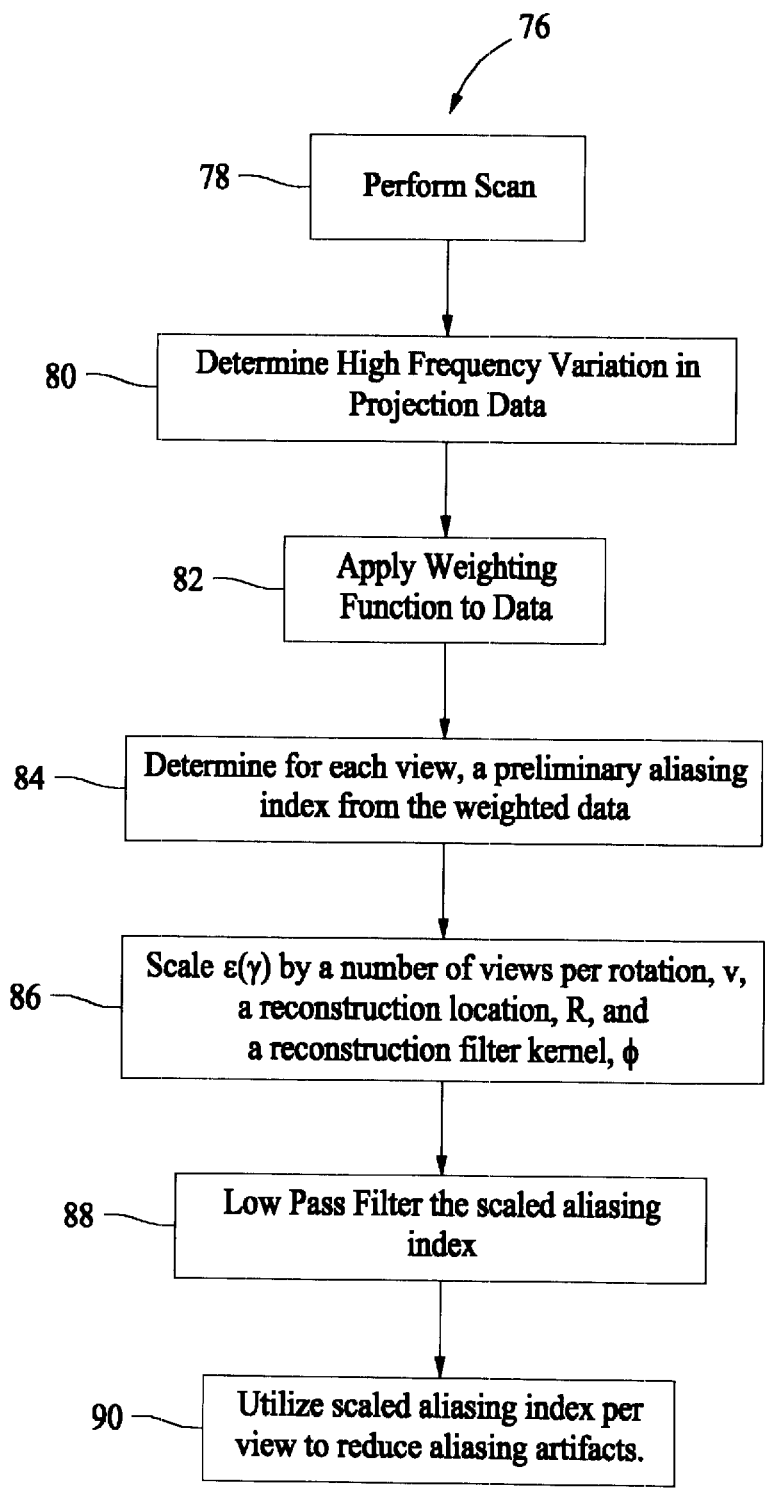
FIG. 6 is a simplified flow chart representative of a suitable adaptive method for synthesizing views of an object.

An example of a suitable adaptive method for synthesizing views is shown in flow chart 76 of FIG. 6, which illustrates steps executed by CT system 10 (shown in FIG. 1) in one embodiment to compensate for view aliasing artifacts. The method illustrated in FIG. 6 can be practiced by DAS 32 (shown in FIG. 2), image reconstructor 34 (shown in FIG. 2), or computer 36 (shown in FIG. 2), or by a combination thereof. Generally, a processor in at least one of DAS 32, reconstructor 34, and computer 36 is programmed to execute the process steps described below.

Referring specifically to FIG. 6, and when performing a scan 78, a set of raw scan data is acquired. The raw scan data is pre-processed to generate a set of projection data $p(\gamma,\beta)$. As explained above, view aliasing occurs when scanned object 22 changes along a plurality of view directions, where each view is determined by a projection angle, $\beta$. Therefore, after collecting the projection data, $p(\gamma,\beta)$, a high frequency variation for each view in the projection data 80 is determined according to the relationship:

$$\xi(\gamma,\beta) = \frac{\partial p(\gamma,\beta)}{\partial \beta},$$

where $p(\gamma,\beta)$ is the measured projection after proper pre-processing, $\gamma$ is the fan angle, $\beta$ is the projection angle, and $\xi(\gamma,\beta)$ represents the high-frequency variation of the projection.

Variations in views collected during a scan can be caused, for example, by patient table 46. Patient table 46 is formed with multiple flat segments, and projection data for the multiple segments changes from view to view. To avoid view variation, a weighting function 82 is applied to high-frequency variation estimate, $\xi(\gamma,\beta)$, to exclude the influence of table 46.

Although many weighting functions can be used, in one embodiment, the boundaries of the weight function, $\gamma_h(\beta)$ and $\gamma_l(\beta)$, are determined based on the location at which the projection intensity exceeds a fraction of the peak value for view $\beta$. Weighting function, $w(\gamma,\beta)$, is zero outside the boundaries and reaches unity at the center region. The transition from zero to unity is a smooth function. For example, an exemplary weighting function, $w(\gamma,\beta)$, can be described by the following relationship:

$$w(\gamma,\beta) = \begin{cases} \frac{\gamma - \gamma_l(\beta)}{\eta} & \gamma_l(\beta) \le \gamma < \gamma_l(\beta)+\eta \\ 1 & \gamma_l(\beta) \le \gamma < \gamma_h(\beta) \\ \frac{\gamma_h(\beta)-\gamma}{\eta} & \gamma_h(\beta)-\eta < \gamma \le \gamma_h(\beta) \\ 0 & \text{otherwise,} \end{cases}$$

where $\eta$ represents the width of a transition region.

In addition to applying weighting function 82, because aliasing artifacts come from the highest frequency contents in the projection, for each view, the maximum value of the frequency content is determined according to the following relationship:

$$\epsilon(\beta)=f[|\xi(\gamma,\beta)w(\gamma,\beta)|],$$

where $f$ is a function representing a maximum frequency value. In another embodiment, $f$ is a function representing the average of a plurality of top N maximum values to reduce the influence of noise. A preliminary aliasing index, $\epsilon(\beta)$, 84 is then determined based on the maximum frequency contents from the weighted data. The amount of aliasing artifacts present in a reconstructed image depends on the frequency contents of the projection, and also on a projection view sampling rate, a reconstruction field of view, and a reconstruction filter kernel. The lower the number of views collected during a $2\pi$ rotation of gantry 12 (shown in FIGS. 1 and 2), the more likely is the occurrence of the presence of an aliasing artifact. Similarly, for the reconstruction region that is further away from an isocenter, the likelihood of aliasing artifacts increases. The reconstruction filter kernel will influence the aliasing artifact in a similar manner, with the higher resolution kernels producing more aliasing. Therefore, the preliminary index, $\epsilon(\beta)$, needs to be scaled 86 by a number of views per rotation, v; a reconstruction location, R; and a reconstruction filter kernel, $\phi$, according to the relationship:

$$\chi(\beta)=g(v^{-1},R,\phi)\epsilon(\beta)$$

To further reduce the influence of noise, the scaled aliasing index is passed through a low pass filter 88.

The scaled and filtered aliasing index, $\chi(\beta)$, is then utilized to reduce aliasing artifacts 90 by determining a region and a number of synthesized views required to minimize potential aliasing artifact. The higher the value of the scaled aliasing index, $\chi(\beta)$, the higher the likelihood of the occurrence of aliasing artifacts. Therefore, a greater number of synthesized views should be generated in regions where the scaled aliasing index is high as compared to regions where the scaled aliasing index is low. The synthesized views can be generated using any one of many known techniques, such as interpolation.

In another embodiment, to minimize aliasing artifact, more contribution, i.e., a higher weight, is placed on the synthesized views if the scaled aliasing index is high in a particular region. In a further alternative embodiment, the aliasing index may be used to predict sampling rates as a function of the projection angle, when DAS 32 (shown in FIG. 2) sampling rate is dynamically adjusted. For instance, the value of the aliasing index increases as DAS 32 sampling rate increases, therefore, a particular sampling rate corresponds to a particular range of aliasing indices.

Computer 36, image reconstructor 34, and/or DAS 32 of imaging system 10, either alone or in combination, provide the processing power necessary to perform the computational steps described above in at least one embodiment of the present invention. Instructions for performing the computational steps are stored in an associated memory, such as mass storage device 38, read only or read/write memory (not shown separately in FIG. 1), or media 52.

In at least one embodiment of the present invention, a computer system separate from imaging system 10 (for example, a workstation, not shown in the figures) is provided to reconstruct images using projection data acquired by imaging system 10. In these embodiments, acquired projection data and corresponding cardiac phase information is transferred from imaging system 10 to the separate computer system via a network (not shown) or suitable media 52. As a free-standing, separate computer system, these embodiments do not require a rotating gantry, a radiation source, or a detector array of their own. Also, these embodiments are configured to read or input projection data previously acquired by a CT imaging system. In other respects, they are configured in manners similar to the other apparatus embodiments discussed herein.

Other embodiments of the present invention include machine readable media 52 having recorded thereon instructions configured to instruct a computer system to perform steps of one or more of the methods described herein.

The above-described embodiments of the present invention will be seen to be effective in reducing aliasing artifacts and increasing spatial resolution at scan rates that would otherwise require increased data acquisition system sampling rates.

While the invention has been described in terms of various specific embodiments, those skilled in the art will recognize that the invention can be practiced with modification within the spirit and scope of the claims.

What is claimed is:

1. A method for reducing aliasing artifacts in a computed tomography system, said method comprising:

scanning an object with a computed tomography system to acquire a projection data set of measured views;

synthesizing additional views of the projection data set utilizing view interpolation; and filtering and backprojecting the projection data set utilizing a weighting function dependent upon parameters $R_f$ and $R_t$, where radius $R_f$ around an isocenter of the CT imaging system is selected in accordance with a low artifact criterion and $R_t$ is a parameter defining a transition region outside of radius $R_f$ around the isocenter of the CT imaging system.

2. A method in accordance with claim 1 wherein the weighting function is different for the measured views and the synthesized views.

3. A method for reducing aliasing artifacts in a computed tomography system, said method comprising:

scanning an object with a computed tomography (CT) imaging system to acquire a projection data set of measured views;

reconstructing a first image utilizing the measured views to produce an image having a central, essentially artifact-free zone;

interpolating views between measured views to produce a projection data set having interpolated views;

reconstructing a second image utilizing both the interpolated views and the measured views; and producing a blended image from the first image and the second image utilizing a weighting function selected to smoothly transition from the first image to the second image in a transition region surrounding an isocenter of the CT imaging system.

4. A method in accordance with claim 3 wherein the first image is written $P_1$ and the second image is written $P_2$, the first image and second image are combined using weighting functions $w_1(i,j)$ and $w_2(i,j)$, and the blended image $P(i,j)$ is written:

$$P(i,j)=w_1(i,j)P_1(i,j)+w_2(i,j)P_2(i,j)$$

where:

$$w_1(i,j)=1-w_2(i,j)$$

and $$w_2(i,j) = \begin{cases} 0 & r \le R_f \\ \dfrac{r-R_f}{R_t-R_f} & R_f < r \le R_t \\ 1 & r > R_t. \end{cases}$$

5. A method in accordance with claim 3 further comprising determining a radius $R_f$ of the central, essentially artifact-free zone.

6. A method in accordance with claim 5 wherein the CT imaging system has a data acquisition system (DAS), and $R_f$ is a function of a sampling rate of the DAS and a scan speed of the CT imaging system.

7. A method in accordance with claim 6 wherein $R_f$ is a distance from the isocenter providing a sampling distance in an azimuthal direction of $50\pi/984$ cm.

8. A method in accordance with claim 3 wherein said interpolating views between measured views comprises synthesizing views uniformly in all directions.

9. A method for reducing aliasing artifacts in a computed tomography system, said method comprising:
   scanning an object with a computed tomography (CT) imaging system to acquire a projection data set of measured views;
   reconstructing a first image utilizing the projection data of measured views set to produce an image having a central, essentially artifact-free zone;
   interpolating views between the measured views to produce a projection data set having interpolated views;
   reconstructing a second image utilizing the interpolated views; and
   producing a blended image from the first image and the second image utilizing a weighting function selected to smoothly transition from the first image to the second image in a transition region surrounding an isocenter of the CT imaging system;
   and further wherein the first image is written $P_1(i,j)$, the second image is written $P_2(i,j)$, pixel $(i,j)$ is a distance r from the isocenter, and images $P_1(i,j)$ and $P_2(i,j)$ are combined by weighting $P_1(i,j)$ and $P_2(i,j)$ with weights $w_1(i,j)$ and $w_2(i,j)$, respectively, where a sum of weights $w_1(i,j)$ and $w_2(i,j)$ is a constant, and $w_2(i,j)$ increases in magnitude relative to $w_1(i,j)$ at least within a transition region in a vicinity of a radius $R_f$ of the central, essentially artifact-free zone.

10. A method in accordance with claim 9 wherein $$w_1(i,j) = 1 - w_2(i,j) \text{ and } w_2(i,j) = \begin{cases} 0, & r \le R_f \\ \dfrac{r - R_f}{2(R_t - R_f)} & R_f < r \le R_t \\ 0.5 & r > R_t, \end{cases}$$

where
r is a distance of pixel $(i,j)$ from the isocenter; and
$R_t$ is a parameter that determines a transition region.

11. A computed tomographic (CT) imaging system having a rotating gantry, a detector array on said rotating gantry, and a radiation source on said rotating gantry configured to project a beam of radiation towards said detector array through an object to be imaged;
   said system configured to:
      scan an object to acquire a projection data set of measured views;
      synthesize additional views of said projection data set utilizing view interpolation; and
      filter and backproject said projection data set utilizing a weighting function dependent upon parameters $R_f$ and $R_t$, where radius $R_f$ around an isocenter of said CT imaging system is selected in accordance with a low artifact criterion and $R_t$ is a parameter defining a transition region outside of radius $R_f$ around said isocenter of said CT imaging system.

12. A system in accordance with claim 11 wherein said weighting function is different for said measured views and said synthesized views.

13. A computed tomographic (CT) imaging system having a rotating gantry, a detector array on said rotating gantry, and a radiation source on said rotating gantry configured to project a beam of radiation towards said detector array through an object to be imaged;
   said system configured to:
      scan an object to acquire a projection data set of measured views;
      reconstruct a first image utilizing said measured views to produce an image having a central, essentially artifact-free zone;
      interpolate views between measured views to produce a projection data set having both interpolated views and said measured views;
      reconstruct a second image utilizing both said interpolated views and said measured views; and
      produce a blended image from said first image and said second image utilizing a weighting function selected to smoothly transition from said first image to said second image in a transition region surrounding an isocenter of said CT imaging system.

14. A system in accordance with claim 13 wherein said first image is written $P_1$ and said second image is written $P_2$, said first image and said second image are combined using weighting functions $w_1(i,j)$ and $w_2(i,j)$, and said blended image $P(i,j)$ is written:

$$P(i,j) = w_1(i,j) P_1(i,j) + w_2(i,j) P_2(i,j)$$

where:

$$w_1(i,j) = 1 - w_2(i,j)$$

and $$w_2(i,j) = \begin{cases} 0 & r \le R_f \\ \dfrac{r - R_f}{R_t - R_f} & R_f < r \le R_t \\ 1 & r > R_t. \end{cases}$$

15. A system in accordance with claim 13 further configured to determine a radius $R_f$ of the central, essentially artifact-free zone.

16. A system in accordance with claim 15 wherein said CT imaging system has a data acquisition system (DAS), and $R_f$ is a function of a sampling rate of said DAS and a scan speed of said CT imaging system.

17. A system in accordance with claim 16 wherein $R_f$ is a distance from said isocenter providing a sampling distance in an azimuthal direction of $50\pi/984$ cm.

18. A system in accordance with claim 13 wherein to interpolate said views between said measured views, said system is configured to synthesize views uniformly in all directions.

19. A computed tomographic (CT) imaging system having a rotating gantry, a detector array on said rotating gantry, and a radiation source on said rotating gantry configured to project a beam of radiation towards said detector array through an object to be imaged;
   said system configured to:
      scan an object to acquire a projection data set of measured views;
      reconstruct a first image utilizing said measured views to produce an image having a central, essentially artifact-free zone;
      interpolate views between said measured views to produce a projection data set of interpolated views;
      reconstruct a second image utilizing said interpolated views; and
      produce a blended image from said first image and said second image utilizing a weighting function selected to smoothly transition from said first image to said second image in a transition region surrounding an isocenter of said CT imaging system;
      and further wherein said first image is written $P_1(i,j)$, said second image is written $P_2(i,j)$, pixel $(i,j)$ is a distance r from said isocenter, and said system is configured to combine said images $P_1(i,j)$ and $P_2(i,j)$ by weighting $P_1(i,j)$ and $P_2(i,j)$ with weights $w_1(i,j)$ and $w_2(i,j)$, respectively, where a sum of said weights $w_1(i,j)$ and $w_2(i,j)$ is a constant, and $w_2(i,j)$ increases in magnitude relative to $w_1(i,j)$ at least within a transition region in a vicinity of a radius $R_f$ of said central, essentially artifact-free zone.

20. A system in accordance with claim 19 wherein $$w_1(i,j) = 1 - w_2(i,j) \text{ and } w_2(i,j) = \begin{cases} 0, & r \le R_f \\ \dfrac{r - R_f}{2(R_t - R_f)} & R_f < r \le R_t \\ 0.5 & r > R_t, \end{cases}$$

where r is a distance of pixel (i,j) from said isocenter; and
$R_t$ is a parameter that determines a transition region.

21. A computer configured to:
read a projection data set of measured views obtained by scanning an object with a computed tomographic (CT) imaging system;
synthesize additional views of the projection data set utilizing view interpolation; and
filter and backproject the projection data set utilizing a weighting function dependent upon parameters $R_f$ and $R_t$, where radius $R_f$ around an isocenter of the CT imaging system is selected in accordance with a low artifact criterion and $R_t$ is a parameter defining a transition region outside of radius $R_f$ around the isocenter of said CT imaging system.

22. A system in accordance with claim 21 wherein said weighting function is different for said measured views and said synthesized views.

23. A computer configured to:
read a projection data set of measured views obtained by scanning an object with a computed tomographic imaging system;
reconstruct a first image utilizing the measured views to produce an image having a central, essentially artifact-free zone;
interpolate views between the measured views to produce a projection data set having interpolated views;
reconstruct a second image utilizing said interpolated views; and
produce a blended image from said first image and said second image utilizing a weighting function selected to smoothly transition from said first image to said second image in a transition region surrounding an isocenter of the CT imaging system.

24. A computer in accordance with claim 23 wherein to reconstruct said second image, said computer is configured to utilize the measured views in addition to said interpolated views; and
said first image is written $P_1$ and said second image is written $P_2$, said first image and said second image are combined using weighting functions $w_1(i,j)$ and $w_2(i,j)$, and said blended image $P(i,j)$ is written:

$$P(i,j) = w_1(i,j)P_1(i,j) + w_2(i,j)P_2(i,j)$$

where:

$$w_1(i,j) = 1 - w_2(i,j)$$

and $$w_2(i,j) = \begin{cases} 0 & r \le R_f \\ \dfrac{r - R_f}{R_t - R_f} & R_f < r \le R_t \\ 1 & r > R_t. \end{cases}$$

25. A computer in accordance with claim 23 further configured to determine a radius $R_f$ of the central, essentially artifact-free zone.

26. A computer in accordance with claim 25 wherein the CT imaging system has a data acquisition system (DAS), and said computer is configured to determine $R_f$ as a function of a sampling rate of the DAS and a scan speed of the CT imaging system.

27. A computer in accordance with claim 26 wherein $R_f$ is a distance from the isocenter providing a sampling distance in an azimuthal direction of $50\pi/984$ cm.

28. A computer in accordance with claim 23 wherein to interpolate said views between the measured views, said computer is configured to synthesize views uniformly in all directions.

29. A computer in accordance with claim 23 wherein said first image is written $P_1(i,j)$, said second image is written $P_2(i,j)$, pixel (i,j) is a distance r from the isocenter, and wherein said computer is configured to combine said images $P_1(i,j)$ and $P_2(i,j)$ by weighting $P_1(i,j)$ and $P_2(i,j)$ with weights $w_1(i,j)$ and $w_2(i,j)$, respectively, where a sum of said weights $w_1(i,j)$ and $w_2(i,j)$ is a constant, and $w_2(i,j)$ increases in magnitude relative to $w_1(i,j)$ at least within a transition region in a vicinity of a radius $R_f$ of said central, essentially artifact-free zone.

30. A computer in accordance with claim 29 wherein $$w_1(i,j) = 1 - w_2(i,j) \text{ and } w_2(i,j) = \begin{cases} 0, & r \le R_f \\ \dfrac{r - R_f}{2(R_t - R_f)} & R_f < r \le R_t \\ 0.5 & r > R_t, \end{cases}$$

where r is a distance of pixel (i,j) from the isocenter; and
$R_t$ is a parameter that determines a transition region.

31. A computer readable medium having instructions recorded thereon configured to instruct a computer to:
read a projection data set of measured views obtained by scanning an object with a computed tomographic (CT) imaging system;
synthesize additional views of the projection data set utilizing view interpolation; and
filter and backproject the projection data set utilizing a weighting function dependent upon parameters $R_f$ and $R_t$, where radius $R_f$ around an isocenter of the CT imaging system is selected in accordance with a low artifact criterion and $R_t$ is a parameter defining a transition region outside of radius $R_f$ around the isocenter of said CT imaging system.

32. A computer readable medium in accordance with claim 31 wherein said weighting function is different for said measured views and said synthesized views.

33. A computer readable medium having instructions recorded thereon configured to instruct a computer to:
read a projection data set of measured views obtained by scanning an object with a computed tomographic imaging system;
reconstruct a first image utilizing the measured views to produce an image having a central, essentially artifact-free zone;

interpolate views between the measured views to produce an projection data set having interpolated views;

reconstruct a second image utilizing said interpolated views; and produce a blended image from said first image and said second image utilizing a weighting function selected to smoothly transition from said first image to said second image in a transition region surrounding an isocenter of the CT imaging system.

34. A computer readable medium in accordance with claim 33 where to reconstruct a second image, said computer readable medium has recorded thereon instructions configured to instruct the computer to utilize the measured views in addition to said interpolated views;

and wherein said first image is written $P_1$ and said second image is written $P_2$, said first image and said second image are combined using weighting functions $w_1(i,j)$ and $w_2(i,j)$, and said blended image $P(i,j)$ is written:

$$P(i,j) w_1(i,j) P_1(i,j) + w_2(i,j) P_2(i,j)$$

where:

$$w_1(i,j) = 1 - w_2(i,j)$$

and $$w_2(i,j) = \begin{cases} 0 & r \leq R_f \\ \dfrac{r - R_f}{R_t - R_f} & R_f < r \leq R_t \\ 1 & r > R_t. \end{cases}$$

35. A computer readable medium in accordance with claim 33 further having instructions recorded thereon configured to instruct a computer to determine a radius $R_f$ of the central, essentially artifact-free zone.

36. A computer readable medium in accordance with claim 35 wherein the CT imaging system has a data acquisition system (DAS), and said computer readable medium further has instructions recorded thereon configured to instruct a computer to determine $R_f$ as a function of a sampling rate of the DAS and a scan speed of the CT imaging system.

37. A computer readable medium in accordance with claim 36 wherein $R_f$ is a distance from the isocenter providing a sampling distance in an azimuthal direction of $50\pi/984$ cm.

38. A computer readable medium in accordance with claim 33 wherein to interpolate said views between the measured views, said computer readable medium has instructions recorded thereon configured to instruct a computer to synthesize views uniformly in all directions.

39. A computer readable medium in accordance with claim 33 wherein said first image is written $P_1(i,j)$, said second image is written $P_2(i,j)$, pixel $(i,j)$ is a distance r from the isocenter, and wherein said computer readable medium has recorded thereon instructions configured to instruct the computer to combine said images $P_1(i,j)$ and $P_2(i,j)$ by weighting $P_1(i,j)$ and $P_2(i,j)$ with weights $w_1(i,j)$ and $w_2(i,j)$, respectively, where a sum of said weights $w_1(i,j)$ and $w_2(i,j)$ is a constant, and $w_2(i,j)$ increases in magnitude relative to $w_1(i,j)$ at least within a transition region in a vicinity of a radius $R_f$ of said central, essentially artifact-free zone.

40. A computer readable medium in accordance with claim 39

$$w_1(i,j) = 1 - w_2(i,j) \text{ and } w_2(i,j) = \begin{cases} 0, & r \leq R_f \\ \dfrac{r - R_f}{2(R_t - R_f)} & R_f < r \leq R_t \\ 0.5 & r > R_t, \end{cases}$$

where r is a distance of pixel $(i,j)$ from the isocenter; and $R_t$ is a parameter that determines a transition region.

* * * * *

UNITED STATES PATENT AND TRADEMARK OFFICE
CERTIFICATE OF CORRECTION

PATENT NO.   : 6,529,574 B1
DATED        : March 4, 2003
INVENTOR(S)  : Jiang Hsieh It is certified that error appears in the above-identified patent and that said Letters Patent is hereby corrected as shown below:

Column 13,
Line 20, delete "$P(i,j)w_1(i,j)P_1(i,j)+w_2(i,j)P_2(i,j)P_2(i,j)$" and insert therefor
-- $P(i,j)=w_1(i,j)P_1(i,j)+w_2(i,j)P_2(i,j)$ --.

Column 14,
Line 26, after "39" insert -- wherein --.

Signed and Sealed this

Twenty-sixth Day of August, 2003

JAMES E. ROGAN
*Director of the United States Patent and Trademark Office*